United States Patent [19]

Bruno

[11] 4,014,317

[45] Mar. 29, 1977

[54] MULTIPURPOSE CARDIOCIRCULATORY ASSIST CANNULA AND METHODS OF USE THEREOF

[75] Inventor: Anthony M. Bruno, Bethesda, Md.

[73] Assignee: The United States of America as represented by the Department of Health, Education and Welfare, Washington, D.C.

[22] Filed: Feb. 18, 1972

[21] Appl. No.: 227,399

[52] U.S. Cl. .............................. 128/1 D; 128/348
[51] Int. Cl.² ................. A61M 25/00; A61B 19/00
[58] Field of Search ............. 128/1 D, 1 R, 2.06 E, 128/3.48, 404, 418, 419 P

[56] References Cited

UNITED STATES PATENTS

| | | | |
|---|---|---|---|
| 3,208,448 | 9/1965 | Woodward | 128/1 D |
| 3,416,534 | 12/1968 | Quinn | 128/419 P |
| 3,478,746 | 11/1969 | Greatbatch | 128/419 P |
| 3,592,184 | 7/1971 | Watkins et al. | 128/1 D |
| 3,707,960 | 1/1973 | Freed | 128/1 D |

Primary Examiner—Dalton L. Truluck
Attorney, Agent, or Firm—Browdy and Neimark

[57] ABSTRACT

A method and device for assisting cardiocirculation includes inserting a cannula in the axillary or subclavian artery, which cannula has associated therewith a blood pump, a balloon pump which responds to EKG signals, and a heart pacer which triggers the EKG and is capable of responding to and reversing ventricular extra systoles, and maneuvering the cannula into the aorta and left ventricle. The device functions by directly unloading surplus blood from the left ventricle of the heart, thereby reducing the work load of the heart so that it may in time recover from a serious if not critical insult.

18 Claims, 5 Drawing Figures

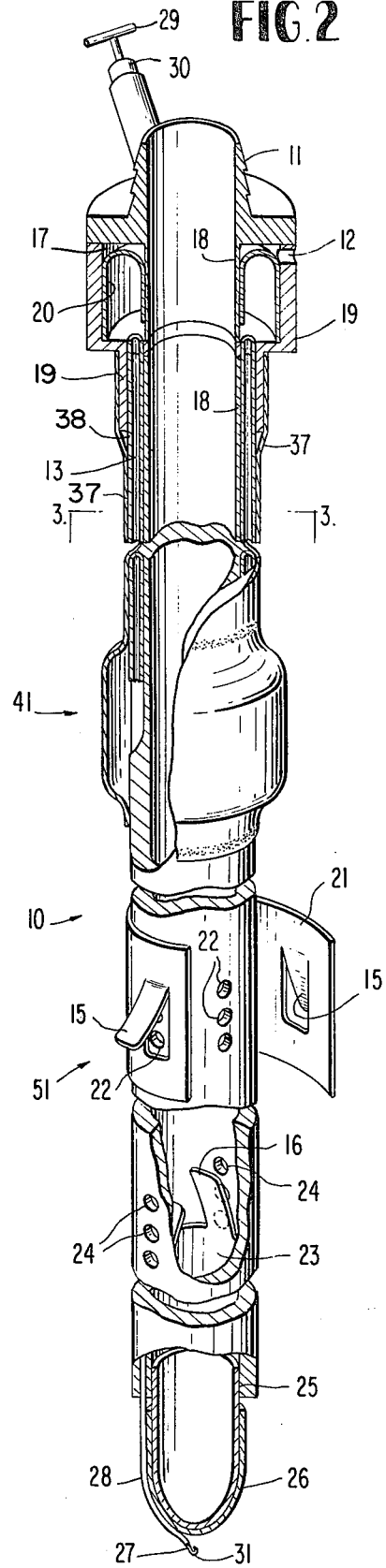

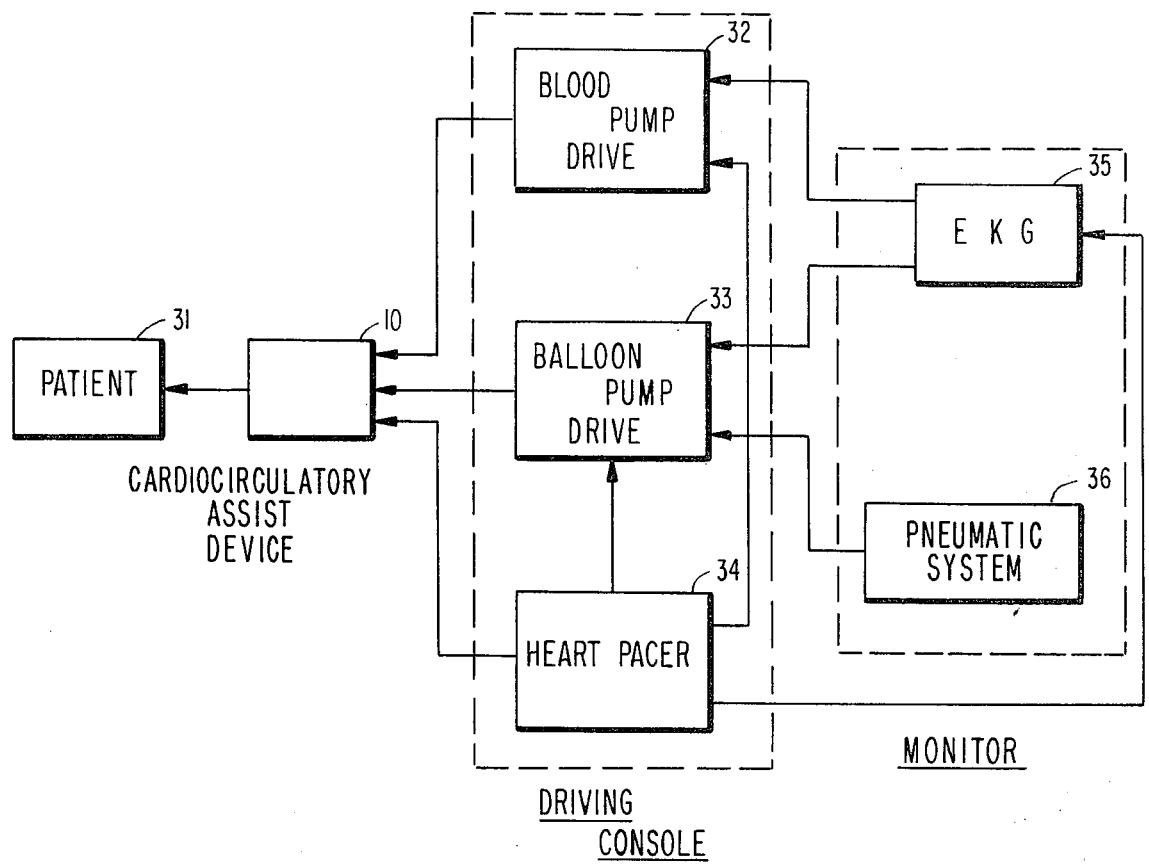

MULTIPURPOSE CARDIOCIRCULATORY ASSIST CANNULA AND METHODS OF USE THEREOF

FIELD OF INVENTION

The present invention relates to a cardiac assisting device and, more particularly, to a multipurpose cardiocirculatory assist cannula.

BACKGROUND OF INVENTION

The clinical management of myocardial failure and impending cardiogenic shock following acute myocardial infarction remains one of the most challenging and important problems facing clinicians. Equally as important is the vexing problem of sudden cardiac death associated with cardiac arrhythmia.

The prevention of such myocardial failure and cardiogenic shock rests upon the consideration of the pathophysiologic mechanism thereof. Metabolic derangements produced by myocardial ischemia result in a profound deterioration of myocardial performance involving dyskinesia. There is a decrease in diastolic compliance of the myocardium as well as a diminished contractile potential. This leads to an increase of end-diastolic and left atrial pressures and volumes. The end result of this cycle is cardiogenic shock and death. In essence inadequate perfusion of an area of myocardium with decreased contractility results in a fall in cardiac output and hypotension. Further deficits in coronary blood flow and extension of myocardial ischemia as a result of the above produces myocardial failure and/or cardiogenic shock.

In many instances, coronary artery disease and/or arterial sclerotic heat disease in themselves must be considered somewhat distinct from the terminal state or its causal relationship to any precipitating factors. The degenerative disease is a result of a progression of perhaps many years' duration. At some point in time, the heart sustains an insult to which it is incapable of adjusting or responding, let alone reversing the process by its own mechanisms and power. cardiocirculatory support and assistance, for whatever period, becomes critical if the system is to be allowed to correct the effects and maintain vital homeostatic processes.

There is still another factor which has played an important, though somewhat elusive role — namely, the question of sudden cardiac death resulting from the effects of uncontrolled and irreversible arrhythmia. Decreased myocardial perfusion resulting from coronary occulsive diseases is believed to be principally responsible for those conditions leading to myocardial catabolic derangements. Acidosis and electrolyte imbalance create a hypersensitive intrinsic conductive mechanism vulnerable to erratic triggering. The end result is often ventricular extrasystoles followed by fatal arrhythmia.

Thus, a heart may be found which already suffers from some degree of degenerative disease of the myocardium and of the coronary arteries including interstitial fibrosis leading to decreased levels of myocardial perfusion. Up to this point and within rather critical limits this heart is capable of carrying on its normal function and responding to increased demands of stress. However, for any number of reasons, at some point in time the scales are tipped and inadequate cardiac output results from the synergistic insult of decreased coronary perfusion coupled with and aggravated by a decrease in the contractile force of the heart. The decreased cardiac output precipitates a vasomotor response leading to increased peripheral resistance. This further aggravates the problem of inadequate cardiac return and of tissue perfusion leading to severe metabolic derangement and as a consequence vasomotor collapse, thus completing the syndrome of the picture of myocardial-circulatory failure.

Whatever triggers the above sequence of events, most investigators agree that the myocardium responding to a compromised circulation (insufficiency of myocardial perfusion) undergoes a somewhat rapid and devolutionary course leading to myocardial failure, cardiogenic shock and death. The other sequence of events is that of cardiac arrhythmia and sudden death.

Prior art cardiac assist pumps such as suggested by Moulapoulas et al. in *American Heart Journal* (1962) Vol. 63, p. 669 and Kantrowitz, U.S. Pat. No. 3,585,983, as well as others, provide an intra-aortic occlusion balloon pumping system. These devices are very important for providing intra-arterial cardiac assistance but are not designed, nor do they accomlish the improvement of myocardial revascularization or the increase of coronary collateral circulation. Furthermore, the presently known counterpulsation devices are based on the phase relationship of the cardiac cycle to the intra-aortic occlusion balloon. Thus, these devices are prone to failure if erratic triggering or cardiac arrhythmia occurs.

SUMMARY OF THE INVENTION

It is therefore an object of the present invention to overcome the deficiencies of the prior art, such as indicated above.

It is another object to provide for inproved cardiac assist.

It is another object of the present invention to provide a multi-purpose cardiocirculatory assist cannula whose capability extends beyond that of existing balloon catheters.

It is still another object of the present invention to provide an improved method of treating cardiocirculatory ailments.

It is another object of the present invention to correct a series of basic and important problems by bringing together in a multiphasic fashion an integral assembly of subsystems in a manner that has never before been attempted.

It is yet another object of the present invention to provide some degree of beneficial effect upon coronary disease and/or associated arteriosclerotic heart disease by increasing collateral circulation and revascularization of the myocardium.

It is still another object of the present invention to interrupt and correct the pathophysiological cycle at different critical points, thus avoiding the devolutionary course of events.

It is still another object of the present invention to provide cardiocirculatory assistance to permit the heart to reestablish its role in the homeostatic life-sustaining processes and thereby prevent failure, shock, and eventual death.

It is still another object of the present invention to provide a device which can be applied quite rapidly using relatively atraumatic surgical techniques requiring minimal intervention.

It is still another object of the present invention to assist the failing heart and circulation during periods of myocardial failure and cardiogenic shock by directly unloading the left ventricle and thereby reducing the workload of the heart.

It is still another object of the present invention to augment coronary perfusion.

It is a further object of the present invention to increase tissue perfusion and, hence, maintain vital organ function.

It is still a further object of the present invention to pace the left ventricle thereby counteracting the effects of arrythmia crises and death while at the same time ensuring proper phasing of the balloon counterpulsation.

These and other objects are accomplished by the present device which involves a cannula, preferably having three functions, which may be inserted into the axillary or subclavian arteries and fed through the aorta until the tip extends into the left ventricle. This cannula (1) acts as a blood pump which withdraws blood from the left ventricle and reinfuses it into the coronary sinuses; (2) it acts as a balloon pump in the aorta to further decrease the workload of the heart; and (3) it acts as a heart pacer which supplies direct ventricular pacing.

Since the myocardium receives most of its blood flow during diastole, the reinfusion of blood via the cannula during this period will increase coronary flow and hence myocardial perfusion pressure. Further, inflation of the balloon at this time augments this flow pressure relationship and hence is optionally effective in assisting the ischemic heart thereby reversing the serious impending catabolic-biochemical imbalance which oftentimes heralds, if not precipitates, arrhythmia. The phase relationship is extremely important to the successful operation of counterpulsation balloon devices of whatever configuration. The present device is capable of dealing with the question by the simple expediency of controlling heart rate and the balloon in such a fashion so as to ensure the proper phasing of each cycle.

The invention will be better understood by consideration of a possible embodiment shown in the drawing, it being understood that this embodiment is exemplary and not limitative.

BRIEF DESCRIPTION OF THE DRAWINGS

The further nature and advantages of the present invention will be more apparent from the following detailed description taken in conjunction with the drawings wherein:

FIG. 1 is an elevational view of the multipurpose cardiocirculatory assist cannula of the present invention;

FIG. 2 is a partly broken away perspective view of the cannula of the present invention;

FIG. 3 is a cross-sectional view through line 3—3 of FIG. 2;

FIG. 4 is a cross-sectional view of another embodiment at a location similar to that of FIG. 3; and FIG. 5 is a block diagram indicating the various subsystems necessary for the complete operation of the present device.

DETAILED DESCRIPTION OF THE PREFERRED EMBODIMENT

The device consists of a cannula 10 (FIGS. 1 & 2) which may be fabricated from reinforced organo-silicon polymers such as Silastic or other blood compatible materials, or at least coated with such a material.

The proximal end of the cannula 10 consists of a nozzle 11 which may advantageously be made of Teflon (polytetrafluoroethylene). The nozzle 11 is designed to allow for quick connection to suitable drive means and consoles (FIG. 5), the nature of which will be clear to those having knowledge of the present field.

Surrounding the base of the nozzle 11 and the housing 18 of the cannula is an outer housing 19. The outer housing 19 around the area at the base of the nozzle 11 is flanged outwardly in order to define an annular chamber 17 around the cannula housing 18. An inlet opening 12 leads through the outer housing 19 for attachment to the pneumatic drive of the balloon control for the balloon section 41 of the device 10. The pneumatic chamber 17 is preferably constructed with an airtight elastic recoil-type diaphragm 20 extending between the housing 18 and outer housing 19 below the inlet opening 12.

Extending distally from the pneumatic chamber 17 is a pneumatic conduit 13 between the housing 18 and the outer housing 19. The conduit 13 may be in the form of small tubes 38 which are held in place on the outside of the housing 18 by outer housing 19 as seen in FIG. 3. In this embodiment the rigid material of outer housing 19 which makes up the wall of chamber 17 is molded to a more flexible material 37 at a point below the chamber 17, which flexible material 37 is laminated to the housing 18 around tubes 38. The flexible material 37 is still considered a part of outer housing 19.

Alternatively, the outer housing 19 can remain rigid all the way to the balloon portion 41 in order to define an annular conduit 39 as seen in FIG. 4. The conduit 13 empties directly into the balloon 14 which has been molded onto the outer surface of the cannula at approximately the midpoint thereof.

If diaphragm 20 were omitted it is apparent that the gas (preferably a low density gas such as $CO_2$) entering opening 12 would pass through chamber 17 and directly into conduit 13 and the balloon portion 41, thereby inflating the balloon 14. In the preferred embodiment, however, a predetermined pressure is sealed into the balloon 14, conduit 13 and chamber 17 up to the diaphragm 20. Gas coming through opening 12 into the chamber 17 will depress elastic diaphragm 20 forcing inflation of the balloon 14. This arrangement prevents the direct flow of gas from the drive means to the balloon 14. Consequently, in the event of accidental rupture of the balloon 14, an excessive amount of gas will not be infused into the artery.

In addition to this safety feature, the use of an elastic diaphragm 20 in the gas chamber 17 will permit almost instantaneous loading and unloading of the balloon 14 and will prevent the balloon 14 from completely collapsing because of the preset pressure therewithin. The balloon 14 therefore will maintain a certain configuration in its deflated mode such that streamlined blood flow around the balloon 14 is provided, thereby avoiding further turbulence to the blood flow. It should be understood that the diaphragm may be placed at any point between the cannula and the gas pump.

Between the balloon 16 and the distal end of the cannula is a blood pump section 51. Here are located several multi-fenestrated unidirectional elastic recoil outlet valves 15. When properly positioned these outlet valves 15 will come to lie within the sinus of Valsalva. The outlet valves 15 are an integral part of a recoil band 21 which is laminated to the cannula housing 18 and is preferably constructed of the same material as the cannula housing 18. A plurality of fenestrae 22 through the cannula housing 18 lead to outlet valves 15.

Between the outlet valves 15 and the distal tip of the cannula lie multi-fenestrated inlet valves 16. The valves 16 are an integral part of a band 23 laminated to the inside diameter of the cannula and cover a plurality of fenestrae 24 through the cannula housing 18. The inlet valves 16 permit blood to be removed from the left ventricle to be subsequently reinfused through the outlet valves 15 into the coronary ostia.

The tip 25 of the cannula 10 is an obturator to permit passage of the device beyond the aortic valves. The tip is preferably made of a methyl methacrylate-type polymer such as Lucite or Plexiglas, possibly coated with a blood compatible material such as Silastic. A pressure transducer 26 may be attached to tip 25 to determine the diastolic pressure within the left ventricle. Suitable electrical leads (not shown) pass through the cannula to a suitable means to translate the signals from the transducer 26.

A pacing electrode 27 is encapsulated within the housing of the cannula 10 in a separate cable 28. The electrode 27 may be advanced independently of the tip of the cannula within cable 28 and may be freely rotated by means of a mechanism located in the area of the inlet nozzle 11. This mechanism is provided with a handle 29 and a plunger 30 which are illustrated schematically in FIG. 2. The tip of the electrode 31 may advantageously be formed in the shape of a grappling hook which opens when the electrode 27 is being extended and closes when it is withdrawn.

Thus the electrode tip 31 may be maneuvered into the optimal position within the ventricle for its pacing function and then secured there by closing the hook onto a fiber of the ventricle wall. When the electrode 27 is eventually removed the fiber may be broken with no adverse effect. Since the electrode 27 is made to operate independently of the cannula 10, once positioned the cannula 10 may be removed from the ventricle while the electrode 27 remains behind for the purpose of pacing the heart. Of course, handle 29 would have to be removed to permit this operation.

FIG. 5 is a block diagram showing the various subsystems for operating the device, as follows:

The blood pump section 51 is provided with suitable driving means 32 located in a console near the patient. Blood is removed through the inlet valve 16 and reinfused through outlet valves 15. The pump and inner lumen may be primed with the patient's blood to begin the pumping operation. Preferably the device should be capable of removing up to 20 cc of blood from the left ventricle and reinfusing the same quantity into the sinus of Valsalva.

The balloon pump 41 is also provided with a driving means 33 located in the console. A pneumatic system 36 is connected thereto for inflating the ballon 14 within a period of time commensurate with the length of time of the cardiac cycle. The actual balloon pumping will be controlled by a delayed mode triggered by the heart pacer 34. The pacer 34 is connected to an electrocardiograph which in turn controls the phases of the blood pump device means 32 and balloon pump drive means 33.

In operation the canula 11 is inserted into any accessable artery leading to the aorta, preferably the axillary or subclavian arteries, through a direct incision necessitating only a minor surgical procedure. It is then passed retrograde so that the tip 25 and the multifenestrated inlet portion 24 as well as the pacing electrode 27 come to lie below the aortic valve within the left ventricle. In this position the outflow tract 15 of the device will be within the sinus of Valsalva thus directing flow into both the left and right coronary orifices.

The balloon 14 will then lie in the transverse aortic arch distal to the carotid outflow tract. The tip of the electrode 31 is maneuvered to the most effective region of the left ventricle and is embedded in place. The most effective place is where the pacer has the best effect as shown by the electrocardiograph 35, which is determined by trail. Once positioned the device is ready to be put into operation.

First, the device can be made simply to unload the left ventricle directly, by withdrawing up to 30 ml. of blood with each stroke and reinfusing this volume into the coronary sinuses during the diastolic phase of the cardiac cycle (pump systole).

Secondly, if it becomes necessary to decrease the workload of the heart further and increase coronary perfusion, the balloon 14 through a separate pneumatic conduit can be utilized. During cardiac diastole the resistance to flow in the vessels of the heart, i.e. the coronary arteries, is at a minimum. Inflation of the balloon 14 at this time increases the flow through the coronary arteries and pumps blood along the aorta toward the neck and head and toward the kidneys, liver, stomach and other organs. Deflation of the balloon 14 at the end of cardiac diastole aids the heart by reducing the pressure in the aorta which the heart must normally pump against during cardiac systole. This permits the heart to pump a large volume of blood with each contraction and also reduces the pressure in the left ventricle at the end of cardiac diastole.

Thirdly, the avoid problems of phase relationship of the device to the cardiac cycle, direct ventricular pacing is simultaneously started by means of the pacing electrode 27 located at the tip of the device.

In summary, the device is versatile enough so that during impending left ventricular failure secondary to myocardial infarction, it can directly unload the left ventricle, perfuse the coronary arteries, reduce the afterload resistance, and pace the left ventricle. As ventricular function improves and the heart is capable of providing a more adequate cardiac output, the cannula can be withdrawn until it lies within the ascending aorta, while the electrode tip remains behind to continue pacing the heart. The operation of the blood pump at this time will be terminated. The left ventricle, once recovered from initial failure may continue to require additional support by way of increased coronary circulation while reducing the afterload resistance and hence cardiac stroke work. The balloon 14 even after partial cannula withdrawal so that the tip of the device no longer protrudes through the aortic valve, will still be positioned within the aortic transverse arch distal to the carotid outflow tract. With proper pacing and positioning the cannula with the balloon can be used as a counter-pulsating device.

In the preferred embodiment, the device measures 50 cm. end-to-end with an outside diameter of about 1.5 cm and an inside diameter of 0.635 cm. The nozzle portion is approximately 4.5 cm. in length. The balloon portion is approximately 25 cm. from the nozzle. The balloon measures about 5 cm. in length and can be inflated to contain about 15 to 20 cc. of gas. The pressure is preset within the diaphragm to approximately half that. When fully inflated the balloon should have a sufficient diameter to occlude the aorta or about 2.5 cm. The outlet valves are located some 15 – 18 cm beyond the balloon and measure approximately 3 cm. in length. The tip of the device is about 7 cm. from the outlet valves of which the final 3 cm. contain the multi-fenestrated inlet valves. The dimensions given above are by no means limitative but are meant to provide an example of workable dimensions for the normal sized human heart and circulatory system. Any dimensions which will permit passage of the cannula through the arteries and the positioning of the various parts in their operative positions are comprehended by the present invention.

It should be understood that the present invention may be fabricated by any presently available techniques. Furthermore, the materials disclosed for the various parts of the cannula are by no means limitative but any biocompatible materials may be used. The pump system used may be any presently available system including pulsatile, non-pulsatile or centrifugal. The other electronic and pneumatic components of the device are well known in the art individually and it is well within the skill of the art to select the proper components which will operate as described herein.

It will be obvious to those skilled in the art that various changes may be made without departing from the scope of the inventin and that the invention is not to be considered limited to what is shown in the drawings and described in the specification.

What is claimed is:
1. A multipurpose cardiocirculatory assist device comprising:
   a hollow elongated cannula having a diameter sufficiently small for insertion into a human artery leading to the aorta, said cannula having a leading tip at the upstream end and a trailing end at the downstream end thereof, wherein upstream and downstream relate to the direction of blood flow during arterial usage;
   electrode means at the leading tip of said cannula for pacing the heart;
   blood pump means to pump blood from the left ventricle during cardiac systole and into the aorta during cardiac diastole, including inlet valve means along said cannula and adapted to be disposed within the left ventricle during usage for allowing blood to pass into said blood pump means, and outlet valve means along said cannula downstream from said inlet valve means and adapted to be disposed within the aorta during usage for allowing blood to pass out of said blood pump means; and
   supplementary heart pumping assist means comprising balloon pump means including a balloon connected to said cannula disposed downstream from said outlet valve means, said balloon pump means causing inflation of said balloon during cardiac diastole and deflation of said balloon during cardiac systole.

2. A cardiocirculatory assist device in accordance with claim 1, wherein said electrode means, blood pump means and supplementary heart pumping assist means include drive means connected thereto for supplying electrical pacing pulses to said electrode means, for driving said blood pump means, and for supplying gas for inflation and deflation of said balloon pump means.

3. A cardiocirculatory assist device in accordance with claim 2, further including:
   a chamber connected between said drive means and said balloon;
   elastic diaphragm means connected within said chamber for preventing gas from said drive means from directly entering said balloon;
   wherein the balloon side of said diaphragm is airtight and has a present pressure therein whereby inflation of said balloon is dependent on the position of said diaphragm means.

4. A cardiocirculatory assist device in accordance with claim 1, wherein said cannula includes multi-fenestrated areas and said inlet valve means and said outlet valve means each comprise one way valves covering the multi-fenestrated areas of said cannula.

5. A cardiocirculatory assist device in accordance with claim 3, further including:
   an outer housing surrounding said cannula between said balloon and the trailing end of said cannula and having a widened portion at the trailing end of said cannula, said chamber being defined by said widened portion of said outer housing, and
   a conduit connecting said chamber and said balloon located between said cannula and said outer housing wherein said conduit comprises at least one tube.

6. A cardiocirculatory assist device in accordance with claim 3, further including:
   an outer housing surrounding said cannula between said balloon and the trailing end of said cannula and having a widened portion at the trailing end of said cannula, said chamber being defined by said widened portion of said outer housing and;
   a conduit connecting said chamber and said balloon located between said cannula and said outer housing wherein said conduit comprises an annular area between said cannula and said outer housing.

7. A cardiocirculatory assist device in accordance with claim 1 wherein said electrode means includes:
   an electrode at the leading tip of said cannula;
   a cable connected to said housing; and
   a lead portion slidably housed in said cable such that said electrode is movable axially and rotatably, independently of said cannula.

8. A cardiocirculatory assist device in accordance with claim 7 wherein said electrode includes securing means connected thereto for securing said electrode in place when in operation.

9. A cardiocirculatory assist device in accordance with claim 2 wherein said drive means further includes electrocardiograph means connected thereto for determining the proper periodicity of operation of said electrode means, blood pump means and supplementary heart pumping assist means.

10. A method of treating cardiocirculatory ailments using the cardiocirculatory assist device of claim 1 comprising the steps of:
   inserting the cannula of said cardiocirculatory assist device into an artery which leads to the aorta;
   maneuvering the cannula into a position in the aorta siuch that the electrode means and the inlet valve means of the cannula lie within the left ventricle, the outlet valve means lies within the sinus of Valsalva and the balloon is in the transverse arc of the aorta distal to the outflow tract of the carotid artery;

supplying electrical pulses through electrode means to ensure a constant heart beat;
pumping blood through the blood pump means; and
driving said supplementary heart pumping assist means, 11. A method in accordance with claim 10 further comprising the steps of:
after ventricular function has improved, ceasing the blood pumping action; and
withdrawing the cannula to a position such that the leading end no longer extends through the aortic valve and the balloon is still within the transverse aortic arch distal to the outflow tract of the carotid artery.

12. A method for augmenting the action of an ailing heart having a left ventricle and associated aorta, comprising:
inserting a catheter tip having spaced apart inlet and outlet check valves thereon into the aorta, through the aortic valve and into the left ventricle, said inlet check valve being located adjacent the tip end of the catheter so that blood may be sucked into the catheter from the left ventricle, said outlet check valve being proximally spaced from the tip end of the catheter so as to be located outside the aortic valve permitting blood within the catheter to be pumped directly into the aorta, said catheter further including supplementary heart pumping assist means comprising balloon pump means including a balloon connected to said catheter proximally spaced from said outlet check valve so as to be located in the transverse arc of the aorta distal to the outflow tract of the carotic artery after said inserting step;
sequentially sucking blood from said left ventricle by way of said inlet valve of the catheter during systolic pulsation and on reverse cycle, forcing all of said sucked blood back through the catheter and into said aorta via said outlet valve; and
inflating said balloon during cardiac diastole and deflating said balloon during systolic pulsation.

13. A method in accordance with claim 12 further comprising the steps of:
after ventricular function has improved, ceasing the blood pumping action; and
withdrawing the catheter to a position such that the tip end no longer extends through the aortic valve and the balloon is still within the transverse aortic arch distal to the outflow tract of the carotid artery.

14. A cardiocirculatory assist device, comprising:
a hollow elongated cannula having a diameter sufficiently small for insertion into a human artery leading to the aorta;
a heart pumping assist means comprising balloon pump means including a balloon connected to said cannula, said balloon pump means causing inflation of said balloon during cardiac diastole and deflation of said balloon during cardiac systole; said heart pumping assist means further including drive means connected to said cannula for supplying gas for inflation and deflation of said balloon pump means;
a chamber connected between said drive means and said balloon; and
elastic diaphragm means connected within said chamber for preventing gas from said drive means from directly entering said balloon, wherein the balloon side of said diaphragm is airtight and has a preset pressure therein whereby inflation of said balloon is dependent on the position of said diaphragm means.

15. A heart assist device for pumping blood directly from the left ventricle into the aorta past the artic vlve, comprising:
catheter means including an elongated member with an axial bore therein and having a distal end for insertion into the left ventricle, said distal end having a tip portion, said tip portion having therein an opening in fluid communication with said bore, said distal end also being provided with a second set of openings axially spaced from said tip opening, said second set of openings also communicating with said bore;
first check valve means associated with said tip opening and closing same during first predetermined intervals and opening same during second predetermined intervals;
second check valve means associated with said second set of openings and closing said second set of openings during said second predetermined intervals and opening same during said first predetermined intervals; and
supplementary heart pumping assist means comprising balloon pump means including a balloon connected to said catheter means proximally spaced from said second check valve means, said balloon pump means causing inflation of said balloon during cardiac diastole and deflation of said balloon during cardiac systole.

16. A heart assist device for pumping blood directly from the left ventricle into the aorta past the aortic valve comprising catheter means including an elongated member with an axial bore therein and having a distal end for insertion into the left ventricle, said distal end having a tip portion, said tip portion having therein an opening in fluid communication with said bore, said distal end also being provided with a second set of openings axially spaced from said top opening, said second set of openings also communicating with said bore, first check valve means associated with said tip opening and closing same during first predetermined intervals and opening same during second predetermined intervals, second check valve means associated with said second set of openings and closing said second set of openings during said second predetermined intervals and opening same during said first predetermined intervals, and channel means within the wall of said catheter means for introducing electrode means through said catheter means directly into the left ventricle.

17. A method for augmenting the action of an ailing heart having a left ventricle and associated aorta, comprising:
inserting a catheter tip having spaced apart inlet and outlet check valves thereon into the aorta, through the aortic valve and into the left ventricle, said inlet check valve being located adjacent the tip end of the catheter so that blood may be sucked into the catheter from the left ventricle, said outlet check valve being proximally spaced from the tip end of the catheter so as to be located outside the aortic valve permitting blood within the catheter to be pumped directly into the aorta, said catheter further including electrode means at the tip end of the catheter for pacing the heart;

sequentialy sucking blood from said left ventricle by way of said inlet valve of the catheter during systolic pulsation and on reverse cycle, forcing all of said sucked blood back through the catheter and into said aorta via said outlet check valve; and supplying electrical pulses through said electrode means to ensure a constant heart beat.

18. A heart assist device for pumping blood directly from the left ventricle into the aorta past the aortic valve, comprising:

catheter means including an elongated member with an axial bore therein and having a distal end for insertion into the left ventricle, said distal end having a tip portion, said tip portion having therein an opening in fluid communication with said bore, said distal end also being provided with a second set of openings axially spaced from said tip opening, said second set of opening also communicating with said bore;

first check valve means associated with said tip opening and closing same during first predetermined intervals and opening same during second predetermined intervals;

second check valve means associated with said second set of openings and closing said second set of openings during said second predetermined intervals and opening same during said first predetermined intervals; and electrode means at the tip portion of said catheter means for pacing the heart.

* * * * *